United States Patent
Snee et al.

(10) Patent No.: US 8,101,430 B2
(45) Date of Patent: Jan. 24, 2012

(54) FLUORESCENT SENSOR BASED ON TWO FLUORESCENT MOIETIES ONE OF WHICH IS A SEMICONDUCTOR NANOCRYSTAL AND METHODS OF USING AND MAKING

(75) Inventors: Preston T. Snee, Chicago, IL (US); Rebecca C. Somers, Cambridge, MA (US); Daniel G. Nocera, Winchester, MA (US); Moungi G. Bawendi, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 575 days.

(21) Appl. No.: 11/990,439

(22) PCT Filed: Aug. 10, 2006

(86) PCT No.: PCT/US2006/031056
§ 371 (c)(1),
(2), (4) Date: Apr. 14, 2009

(87) PCT Pub. No.: WO2007/021757
PCT Pub. Date: Feb. 22, 2007

(65) Prior Publication Data
US 2009/0221088 A1    Sep. 3, 2009

Related U.S. Application Data

(60) Provisional application No. 60/707,979, filed on Aug. 15, 2005.

(51) Int. Cl.
*G01N 33/543*    (2006.01)

(52) U.S. Cl. ........ 436/518; 436/164; 436/166; 436/172; 422/81; 422/82.05; 422/82.06; 422/82.07

(58) Field of Classification Search .................. None
See application file for complete search history.

(56) References Cited

U.S. PATENT DOCUMENTS

| | | | |
|---|---|---|---|
| 6,207,229 B1 | 3/2001 | Bawendi et al. |
| 6,207,392 B1 | 3/2001 | Weiss et al. |
| 6,251,303 B1 | 6/2001 | Bawendi et al. |
| 6,306,610 B1 | 10/2001 | Bawendi et al. |
| 6,319,426 B1 | 11/2001 | Bawendi et al. |
| 6,322,901 B1 | 11/2001 | Bawendi et al. |
| 6,326,144 B1 | 12/2001 | Bawendi et al. |
| 6,330,464 B1 | 12/2001 | Colvin, Jr. et al. |
| 6,444,143 B2 | 9/2002 | Bawendi et al. |
| 6,576,291 B2 | 6/2003 | Bawendi et al. |
| 6,607,829 B1 | 8/2003 | Bawendi et al. |
| 6,821,337 B2 | 11/2004 | Bawendi et al. |
| 6,828,179 B2 | 12/2004 | Yamazaki et al. |

(Continued)

OTHER PUBLICATIONS

Clapp et al. "Fluorescence Resonance Energy Transfer Between Quantum Dot Donors and Dye-Labeled Protein Acceptors", J. Am. Chem. Soc. 2004, v. 126, pp. 301-310.*

(Continued)

*Primary Examiner* — Yelena G Gakh
(74) *Attorney, Agent, or Firm* — Steptoe & Johnson LLP

(57) ABSTRACT

Binding an analyte can cause a change in fluorescence emission of a sensor. The change in fluorescence can be related to the amount of analyte present. The sensor can include a semiconductor nanocrystal linked to a fluorescent moiety. Upon excitation, the fluorescent moiety can transfer energy to the semiconductor nanocrystal, or vice versa.

30 Claims, 5 Drawing Sheets

U.S. PATENT DOCUMENTS

| | | |
|---|---|---|
| 6,861,155 B2 | 3/2005 | Bawendi et al. |
| 6,921,496 B2 | 7/2005 | Anderson et al. |
| 7,060,252 B2 | 6/2006 | Barbera-Guillem |
| 7,160,613 B2 | 1/2007 | Bawendi et al. |
| 2002/0102586 A1* | 8/2002 | Ju et al. ............................ 435/6 |
| 2005/0019486 A1 | 1/2005 | Barbera-Guillem |

OTHER PUBLICATIONS

Ballou et al. "Noninvasive Imaging of Quantum Dots in Mice", Bioconjugate Chem. 2004, v. 15, pp. 79-86.*

* cited by examiner

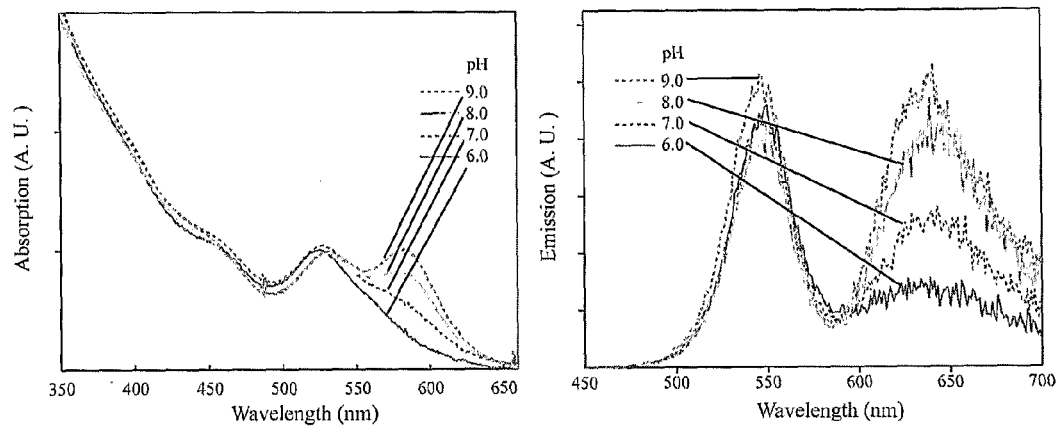
FIG. 4A  FIG. 4B
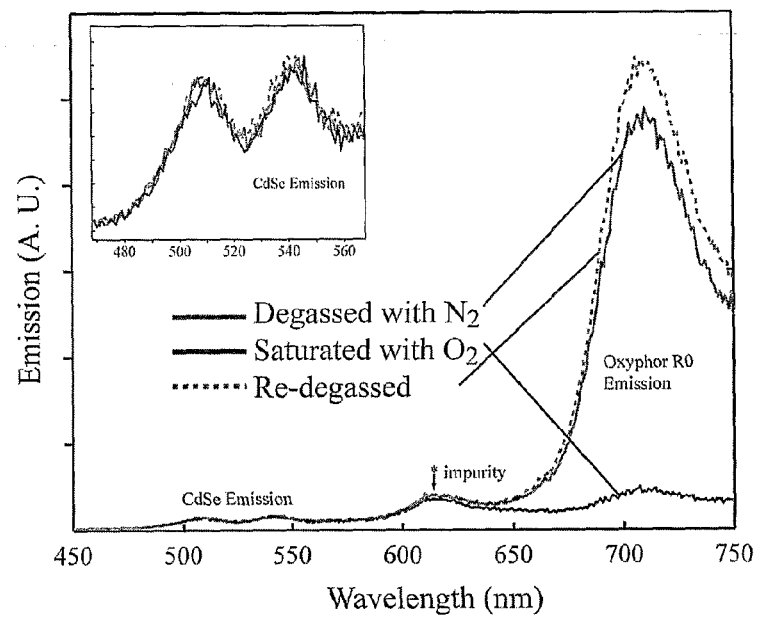
FIG. 5

FLUORESCENT SENSOR BASED ON TWO FLUORESCENT MOIETIES ONE OF WHICH IS A SEMICONDUCTOR NANOCRYSTAL AND METHODS OF USING AND MAKING

CLAIM OF PRIORITY

This application claims priority under 35 USC 371 to International Application No. PCT/IB2006/031056, filed on Aug. 10, 2006, which claims priority to U.S. Provisional Application Ser. No. 60/707,979, filed Aug. 15, 2005, each of which is incorporated by reference in its entirety.

FEDERALLY SPONSORED RESEARCH OR DEVELOPMENT

This invention was made with government support under Grant No. CHE0209898 awarded by the NSF, and grant number KK1043, awarded by the ARO. The government has certain rights in the invention.

TECHNICAL FIELD

The invention relates to a fluorescent sensor, and methods of making and using the sensor.

BACKGROUND

A fluorescent sensor can produce a detectable change in fluorescence response upon interacting with an analyte. Fluorescent sensors can provide desirable properties such as water solubility, low detection limits, and high selectivity for a desired analyte The analyte can be a small molecule or ion (such as, for example, $H^+$ (i.e., pH), $Ca^{2+}$; glucose, or $O_2$).

SUMMARY

Semiconductor nanocrystals can be conjugated to energy-donor or energy-acceptor molecules for chemosensing by the Förster Resonance Energy Transfer (FRET) mechanism. The semiconductor nanocrystal can be rendered water soluble by a functionalized polymer, which also provides a framework to chemically attach dyes and receptors that are useful for chemosensing and bio-labeling studies.

The nanocrystal can be excited by illumination with an excitation wavelength of light. The conjugated dye molecule absorbs energy from an excited nanocrystal via the FRET mechanism and emits light in turn. Binding of an analyte that affects the absorption intensity of the conjugated dye molecule will modulate the FRET efficiency of energy transfer from the nanocrystal to the dye. As a consequence, the ratio of the nanocrystal emission to dye emission is modulated by the presence of targeted analytes. Alternatively, the dye can be excited by the excitation wavelength and transfer energy to the nanocrystal. An isosbestic point observed in the emission spectrum of the dye-nanocrystal conjugate is evidence of the FRET interaction, and allows for ratiometric sensing. The conjugates advantageously have many of the positive characteristics of the nanocrystal, such as excitation at a broad range of wavelengths, long fluorescence lifetime, and high photostability. A variety of biological or chemical moieties can be attached to the conjugate, which can allow the conjugate to be targeted to a desired location within a variety of environments and simultaneously report the presence of the analyte.

In one aspect, a composition includes a first fluorescent moiety and a second fluorescent moiety associated with the first fluorescent moiety. The first fluorescent moiety is capable of transferring energy to the second fluorescent moiety when excited. The first fluorescent moiety or the second fluorescent moiety can include a semiconductor nanocrystal. The second fluorescent moiety can be capable of binding an analyte. The first fluorescent moiety can include a semiconductor nanocrystal. An emission intensity of the second fluorescent moiety can be altered when second fluorescent moiety binds the analyte.

In another aspect, a method of detecting an analyte includes illuminating a composition with an excitation wavelength and measuring a fluorescent emission of the composition. The composition includes a first fluorescent moiety and a second fluorescent moiety associated with the first fluorescent moiety. The first fluorescent moiety is capable of transferring energy to the second fluorescent moiety when excited. The first fluorescent moiety or the second fluorescent moiety includes a semiconductor nanocrystal.

Measuring a fluorescent emission of the composition can include measuring a fluorescence emission intensity at an emission wavelength of the first fluorescent moiety, or measuring a fluorescence emission intensity at an emission wavelength of the second fluorescent moiety. Measuring a fluorescent emission of the composition can include measuring a ratio of a fluorescence emission intensity of the first fluorescent moiety to a fluorescence emission intensity of the second fluorescent moiety. A ratio can be measured between a fluorescence emission intensity of the first fluorescent moiety to a fluorescence emission intensity of the emissive isosbestic point for the composition or between a fluorescence emission intensity of the second fluorescent moiety to the fluorescence emission intensity of the emissive isosbestic point for the composition. The method can include relating the measured ratio to a concentration of the analyte.

In another aspect, a method of making a composition includes linking a first fluorescent moiety to a second fluorescent moiety, wherein the first fluorescent moiety or the second fluorescent moiety includes a semiconductor nanocrystal. After linking, the first fluorescent moiety can be capable of transferring energy to the second fluorescent moiety, when the first fluorescent moiety is excited.

The semiconductor nanocrystal can include an outer layer including a compound linked to a surface of the nanocrystal and having a first hydrophobic region. The composition can include an amphiphilic compound having a second hydrophobic region interacting with the first hydrophobic region. The amphiphilic compound can be linked to the first fluorescent moiety. The amphiphilic compound can be linked to a plurality of fluorescent moieties.

The semiconductor nanocrystal includes a core including a first semiconductor material. The semiconductor nanocrystal can include an overcoating on a surface of the core including a second semiconductor material. The semiconductor nanocrystal includes an second overcoating on a surface of the overcoating including a third semiconductor material.

The semiconductor nanocrystal can include an outer layer including a compound linked to a surface of the nanocrystal and having a first hydrophobic region. Linking can includes contacting the semiconductor nanocrystal with an amphiphilic compound having a second hydrophobic region. The method can include linking the second fluorescent moiety to the amphiphilic compound. The amphiphilic compound can be linked to the second fluorescent moiety. The semiconductor nanocrystal can include an outer layer including a polymer, such as an amphiphilic polymer, a polyethylene glycol or a dendrimer. In certain embodiments, the semiconductor nanocrystal can include a ZnSe or CdZnS core.

Linking can include contacting the semiconductor nanocrystal with a compound including a coordinating group having an affinity for a surface of the semiconductor nanocrystal, and a fluorescent moiety, or coupling a surface of the nanocrystal and the second fluorescent moiety with a polyethylene glycol or a dendrimer The semiconductor nanocrystal can include an outer layer including a compound having a first reactive functional group. Linking can include contacting the semiconductor nanocrystal with a compound including a second reactive functional group capable of reacting with the first reactive functional group to form a bond, and a fluorescent moiety.

Other features, objects and advantages will be apparent from the description, the drawings and the claims.

BRIEF DESCRIPTION OF THE DRAWINGS

FIGS. 4A and 4B are graphs displaying optical properties of a fluorescent sensor.

FIG. 5 is a graph displaying optical properties of a fluorescent sensor.

DETAILED DESCRIPTION

Figure 1A:
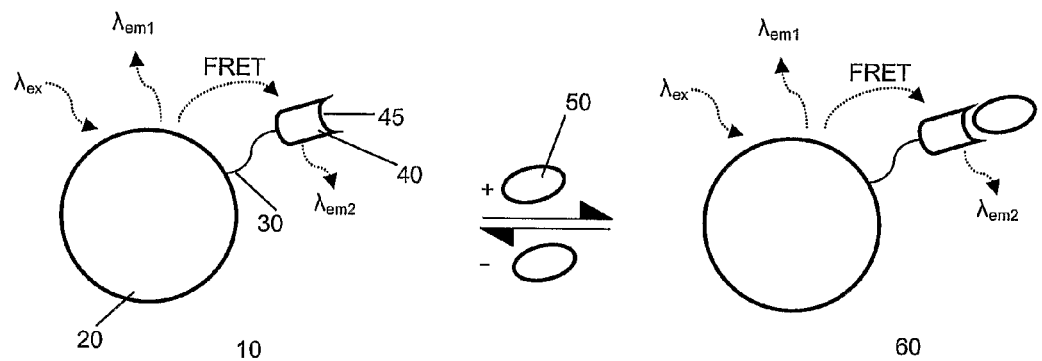
FIGS. 1A and 1B are schematic illustrations of a fluorescent sensor.

Förster resonance energy transfer (sometimes referred to as fluorescence resonance energy transfer, or simply "FRET") occurs when a fluorescent moiety (or fluorophore) absorbs light energy at its excitation wavelength. The energy absorbed is subsequently released through various pathways, one being emission of photons to produce fluorescence at an emission wavelength (longer than the excitation wavelength). Another pathway is radiationless energy transfer, process by which the energy of the excited state of one fluorescent moiety is transferred, without actual photon emission, to a second fluorescent moiety. The second fluorescent moiety, now in an excited state, may then release energy at its emission wavelength. The first fluorescent moiety is generally termed the donor (D) and has an excited state of higher energy than that of the second fluorescent moiety, termed the acceptor (A). For FRET to occur efficiently, the emission spectrum of the donor must overlap with the excitation spectrum of the acceptor, and the donor and acceptor be sufficiently close. The distance over which radiationless energy transfer is effective depends on many factors, including the fluorescence quantum efficiency of the donor, the extinction coefficient of the acceptor, the degree of overlap of their respective spectra, the refractive index of the medium, and the relative orientation of the transition moments of the two fluorescent moieties, but is typically 4-6 nm for favorable pairs of donor and acceptor. Beyond the optimum range of intermolecular distances, the energy transfer efficiency falls off as the inverse sixth power of the distance.

A fluorescent sensor can utilize FRET to measure the concentration of an analyte. The sensor includes two distinct fluorescent moieties, each having emission and excitation spectra. The fluorescent moieties are chosen such that the excitation spectrum of one of the moieties (the acceptor moiety) overlaps with the emission spectrum of the other fluorescent moiety (the donor moiety). When the donor moiety is excited by an excitation wavelength of light, the sensor can undergo FRET: the donor moiety donates energy from its excited state to the acceptor moiety. The acceptor moiety can then return to its ground state by emitting energy as an emission wavelength of light.

The donor and acceptor fluorescent moieties are linked together in the sensor. The link is chosen to keep the donor and acceptor close enough for efficient FRET to occur. One of the moieties is selected to interact with an analyte (e.g., bind to the analyte). Typically, the donor moiety can interact with the analyte; however, the sensor can be prepared such that the acceptor moiety interacts with the analyte. Binding of the analyte by the donor (or acceptor) moiety leads to a change in fluorescence properties of the donor (or acceptor) moiety. In particular, binding the analyte can change the excitation spectrum, emission spectrum, quantum yield, excited state lifetime, or another fluorescence property of the donor moiety. The change can be detected as a change in the ratio of the amount of light emitted by the donor and acceptor fluorescent moieties. The ratio of emission intensities between the two emission wavelengths provides a measure of the concentration of the analyte in the sample, which is based in part on the binding affinity of the binding moiety and the analyte. Alternatively, the ratio of the amount of light emitted by the donor moiety and the emissive isosbestic point or the acceptor moiety with the emissive isosbestic point can also provide a measure of the concentration of the analyte in the sample. As the isosbestic point is the one constant point in the entire emission profile of the donor-acceptor pair, it allows the construct to be self-referencing.

The efficiency of FRET depends on the separation distance and the orientation of the donor and acceptor fluorescent moieties. For example, the Förster equation describes the efficiency of excited state energy transfer, based in part on the fluorescence quantum yield of the donor moiety and the energetic overlap with the acceptor moiety. The Förster equation is:

$$E = \frac{F_0 - F}{F_0} = \frac{R_0^6}{(R^6 + R_0^6)}$$

where E is the efficiency of FRET, F and $F_0$ are the fluorescence intensities of the donor moiety in the presence and absence of the acceptor, respectively, and R is the distance between the donor moiety and the acceptor moiety.

The characteristic distance $R_0$ at which FRET is 50% efficient depends on the quantum yield of the donor moiety (i.e., the shorter-wavelength fluorophore), the extinction coefficient of the acceptor moiety (i.e., the longer-wave-length fluorophore), and the overlap between the emission spectrum of the donor moiety and the excitation spectrum of the acceptor moiety. $R_0$ is given (in angstroms) by $$R_0 = 9.79 \times 10^3 (K^2 Q J n^{-4})^{1/6}$$

where $K^2$ is an orientation factor having an average value close to 0.67 for freely mobile donors and acceptors, Q is the quantum yield of the unquenched donor moiety, n is the refractive index of the medium separating the donor moiety and the acceptor moiety, and J is the overlap integral. J can be quantitatively expressed as the degree of spectral overlap between the donor moiety and the acceptor moiety according to the equation:

$$J = \frac{\int_0^\infty F_D(\lambda)\varepsilon_A(\lambda)\lambda^4 d\lambda}{\int_0^\infty F_D(\lambda)d\lambda}$$

where $\varepsilon_A(\lambda)$ ($M^{-1}$ $cm^{-1}$) is the molar absorptivity of the acceptor and $F_\lambda$ is the donor moiety fluorescence intensity at wavelength λ. See, for example, Förster, T. Ann. Physik 2:55-75 (1948), which is incorporated by reference in its entirety. Tables of spectral overlap integrals are readily available to those working in the field (for example, Berlman, I. B. Energy transfer parameters of aromatic compounds, Academic Press, New York and London (1973), which is incorporated by reference in its entirety). FRET is a nondestructive spectroscopic method that can monitor proximity and relative angular orientation of fluorophores in living cells. See, for example, Adams, S. R., et al., Nature 349:694-697 (1991), and Gonzalez, J. & Tsien, R. Y. Biophys. J. 69:1272-1280 (1995), each of which is incorporated by reference in its entirety.

These factors need to be balanced to optimize the efficiency and detectability of FRET from the fluorescent indicator. The emission spectrum of the donor fluorescent moiety should overlap as much as possible with the excitation spectrum of the acceptor fluorescent moiety to maximize the overlap integral J. Also, the quantum yield of the donor fluorescent moiety and the extinction coefficient of the acceptor fluorescent moiety should be as large as possible to maximize $R_0$. In addition, the excitation spectra of the donor and acceptor moieties should overlap as little as possible so that a wavelength region can be found at which the donor moiety can be excited selectively and efficiently without directly exciting the acceptor moiety. Direct excitation of the acceptor moiety should be avoided since it can be difficult to distinguish direct emission from fluorescence arising from FRET. Similarly, the emission spectra of the donor and acceptor moieties should have minimal overlap so that the two emissions can be distinguished. High fluorescence quantum yield of the acceptor moiety is desirable if the emission from the acceptor moiety is to be monitored to determine analyte concentration in a sample.

The amount of analyte in a sample can be determined by determining the degree of FRET in the sample. Changes in analyte concentration can be determined by monitoring FRET at a first and second time after contact between the sample and the fluorescent indicator and determining the difference in the degree of FRET. The amount of analyte in the sample can be calculated by using a calibration curve established by titration.

The degree of FRET can be determined by any spectral or fluorescence lifetime characteristic of the excited donor moiety. For example, intensity of the fluorescent signal from the donor, the intensity of fluorescent signal from the acceptor, the ratio of the fluorescence amplitudes near the acceptor's emission maxima to the fluorescence amplitudes near the donor's emission maximum, or the excited state lifetime of the donor can be monitored.

Preferably, changes in the degree of FRET are determined as a function of the change in the ratio of the amount of fluorescence from the donor and acceptor moieties, a process referred to as "ratioing." Changes in the absolute amount of indicator, excitation intensity, and turbidity or other background absorbances in the sample at the excitation wavelength affect the intensities of fluorescence from both the donor and acceptor approximately in parallel. Therefore the ratio of the two emission intensities or the ratio of one of the fluorescent moiety to the emissive isosbestic point are more robust and preferred measures of analyte concentration than either intensity alone.

Fluorescence in a sample is measured using a fluorometer. In general, excitation radiation, from an excitation source having a first wavelength, passes through excitation optics. The excitation optics cause the excitation radiation to excite the sample. In response, fluorescent moieties in the sample emit radiation which has a wavelength that is different from the excitation wavelength. Collection optics then collect the emission from the sample. The device can include a temperature controller to maintain the sample at a specific temperature while it is being scanned. For high-throughput applications, the fluorometer can include a multi-axis translation stage to move a microtiter plate holding a plurality of samples in order to position different wells to be exposed. The multi-axis translation stage, temperature controller, auto-focusing feature, and electronics associated with imaging and data collection can be managed by an appropriately programmed digital computer. The computer also can transform the data collected during the assay into another format for presentation.

Methods of performing assays on fluorescent materials are well known in the art and are described in, e.g., Lakowicz, J. R., Principles of Fluorescence Spectroscopy, New York: Plenum Press (1983); Herman, B., Resonance energy transfer microscopy, in: Fluorescence Microscopy of Living Cells in Culture, Part B, Methods in Cell Biology, vol. 30, ed. Taylor, D. L. & Wang, Y.-L., San Diego: Academic Press (1989), pp. 219-243; and Turro, N. J., Modern Molecular Photochemistry, Menlo Park: Benjamin/Cummings Publishing Col, Inc. (1978), pp. 296-361, each of which is incorporated by reference in its entirety. In addition to single-photon excited fluorescence microscopy, a method can include multi-photon laser scanning microscopy (MPLSM), for example, as described in Webb et al., Science 300:1434 (2003) and Denk et al. Nature Methods 2:932 (2005), each of which is incorporated by reference in its entirety. Because of the large two-photon absorption cross-section that semiconductor nanocrystals possess, the nanocrystals can be used in biological environments via multi-photon laser scanning microscopy, which extends the reach of in vivo fluorescence imaging to depths as great as 700 microns and limits photodegradation of the sensing dyes by reducing the excitation volume.

The excited state lifetime of the donor moiety is, likewise, independent of the absolute amount of material, excitation intensity, or turbidity or other background absorbances. Its measurement requires equipment with nanosecond time resolution.

Quantum yields of fluorescent compositions can be estimated by comparison with fluorescein in 0.1 N NaOH as a standard of quantum yield 0.91. See, for example, J. N. Miller, ed., Standards in Fluorescence Spectrometry, New York: Chapman and Hall (1981), which is incorporated by reference in its entirety.

Figure 1B:
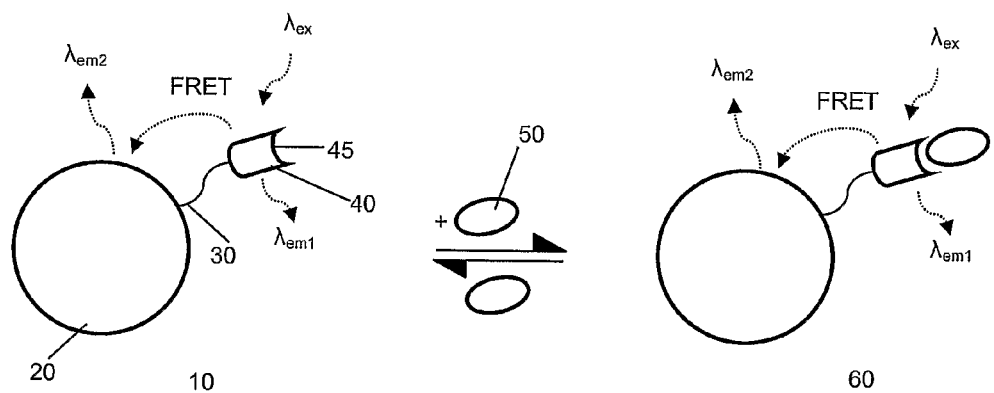

Referring to FIG. 1, sensor 10 includes a fluorescent moiety 20 linked by linker 30 to a distinct fluorescent moiety 40. Linker 30 can be chosen to ensure that the distance between moieties 20 and 40 allows for efficient FRET between 20 and 40. Fluorescent moiety 40 includes recognition feature 45. Recognition feature 45 is capable of binding analyte 50, to form complex 60. In FIG. 1A, fluorescent moiety 20 is the donor and fluorescent moiety 40 is the acceptor. In contrast, FIG. 1B shows sensor 10 when fluorescent moiety 40 is the donor and fluorescent moiety 20 is the acceptor. Illumination of sensor 10 with an excitation wavelength of light ($\lambda_{ex}$) excites the donor. The donor can emit light at its emission wavelength ($\lambda_{em1}$) or undergo FRET to excite the acceptor (other mechanisms of excited state decay are possible, but are not illustrated in FIG. 1). Once excited, the acceptor can emit light at its emission wavelength ($\lambda_{em2}$). Binding of analyte 50 to recognition feature 45 can alter the fluorescence properties of fluorescent moiety 40, such as absorption of the excitation wavelength, emission of light, or efficiency of FRET (e.g., the value of overlap integral J). Preferably, binding of analyte 50 to recognition feature 45 alters the ratio of light emitted at $\lambda_{em1}$ compared to light emitted at $\lambda_{em2}$.

Fluorescent moiety 20 can be a semiconductor nanocrystal. Semiconductor nanocrystals can have properties advantageous for sensor applications, such as a broad excitation spectrum, a narrow emission spectrum, and high photostability. Nanocrystals having a desired emission wavelength can be prepared by selecting appropriate semiconductor materials and nanocrystal sizes. Nanocrystal surfaces can be modified with an organic layer to provide desired solubility, reactivity, or other properties.

Preparation of Semiconductor Nanocrystals, and their Advantageous Fluorescence properties, are described in, for example, U.S. Pat. Nos. 6,322,901; 6,207,229; 6,326,144; 6,306,610; 6,251,303; 6,319,426; 6,444,143; 6,607,829; 6,861,155; 6,576,291; and 6,821,337, each of which is incorporated by reference in its entirety.

The method of manufacturing a nanocrystal is a colloidal growth process. See, for example, U.S. Pat. Nos. 6,322,901 and 6,576,291, each of which is incorporated by reference in its entirety. Colloidal growth occurs by rapidly injecting an M-containing compound and an X donor into a hot coordinating solvent. The coordinating solvent can include an amine. The M-containing compound can be a metal, an M-containing salt, or an M-containing organometallic compound. The injection produces a nucleus that can be grown in a controlled manner to form a nanocrystal. The reaction mixture can be gently heated to grow and anneal the nanocrystal. Both the average size and the size distribution of the nanocrystals in a sample are dependent on the growth temperature. The growth temperature necessary to maintain steady growth increases with increasing average crystal size. The nanocrystal is a member of a population of nanocrystals. As a result of the discrete nucleation and controlled growth, the population of nanocrystals obtained has a narrow, monodisperse distribution of diameters. The monodisperse distribution of diameters can also be referred to as a size. The process of controlled growth and annealing of the nanocrystals in the coordinating solvent that follows nucleation can also result in uniform surface derivatization and regular core structures. As the size distribution sharpens, the temperature can be raised to maintain steady growth. By adding more M-containing compound or X donor, the growth period can be shortened.

The M-containing salt is a non-organometallic compound, e.g., a compound free of metal-carbon bonds. M is cadmium, zinc, magnesium, mercury, aluminum, gallium, indium or thallium. The M-containing salt can be a metal halide, metal carboxylate, metal carbonate, metal hydroxide, metal oxide, or metal diketonate, such as a metal acetylacetonate. The M-containing salt is less expensive and safer to use than organometallic compounds, such as metal alkyls. For example, the M-containing salts are stable in air, whereas metal alkyls a generally unstable in air. M-containing salts such as 2,4-pentanedionate (i.e., acetylacetonate (acac)), halide, carboxylate, hydroxide, or carbonate salts are stable in air and allow nanocrystals to be manufactured under less rigorous conditions than corresponding metal alkyls.

Suitable M-containing salts include cadmium acetylacetonate, cadmium iodide, cadmium bromide, cadmium hydroxide, cadmium carbonate, cadmium acetate, cadmium oxide, zinc acetylacetonate, zinc iodide, zinc bromide, zinc hydroxide, zinc carbonate, zinc acetate, zinc oxide, magnesium acetylacetonate, magnesium iodide, magnesium bromide, magnesium hydroxide, magnesium carbonate, magnesium acetate, magnesium oxide, mercury acetylacetonate, mercury iodide, mercury bromide, mercury hydroxide, mercury carbonate, mercury acetate, aluminum acetylacetonate, aluminum iodide, aluminum bromide, aluminum hydroxide, aluminum carbonate, aluminum acetate, gallium acetylacetonate, gallium iodide, gallium bromide, gallium hydroxide, gallium carbonate, gallium acetate, indium acetylacetonate, indium iodide, indium bromide, indium hydroxide, indium carbonate, indium acetate, thallium acetylacetonate, thallium iodide, thallium bromide, thallium hydroxide, thallium carbonate, or thallium acetate.

Prior to combining the M-containing salt with the X donor, the M-containing salt can be contacted with a coordinating solvent form an M-containing precursor. Typical coordinating solvents include alkyl phosphines, alkyl phosphine oxides, alkyl phosphonic acids, or alkyl phosphinic acids, however, other coordinating solvents, such as pyridines, furans, and amines may also be suitable for the nanocrystal production. Examples of suitable coordinating solvents include pyridine, tri-n-octyl phosphine (TOP) and tri-n-octyl phosphine oxide (TOPO). Technical grade TOPO can be used. The coordinating solvent can include a 1,2-diol or an aldehyde. The 1,2-diol or aldehyde can facilitate reaction between the M-containing salt and the X donor and improve the growth process and the quality of the nanocrystal obtained in the process. The 1,2-diol or aldehyde can be a $C_6$-$C_{20}$ 1,2-diol or a $C_6$-$C_{20}$ aldehyde. A suitable 1,2-diol is 1,2-hexadecanediol and a suitable aldehyde is dodecanal.

The X donor is a compound capable of reacting with the M-containing salt to form a material with the general formula MX. Typically, the X donor is a chalcogenide donor or a pnictide donor, such as a phosphine chalcogenide, a bis(silyl) chalcogenide, dioxygen, an ammonium salt, or a tris(silyl) pnictide. Suitable X donors include dioxygen, elemental sulfur, bis(trimethylsilyl) selenide (($TMS)_2Se$), trialkyl phosphine selenides such as (tri-n-octylphosphine) selenide (TOPSe) or (tri-n-butylphosphine) selenide (TBPSe), trialkyl phosphine tellurides such as (tri-n-octylphosphine) telluride (TOPTe) or hexapropylphosphorustriamide telluride (HPPTTe), bis(trimethylsilyl)telluride (($TMS)_2Te$), sulfur, bis(trimethylsilyl)sulfide (($TMS)_2S$), a trialkyl phosphine sulfide such as (tri-n-octylphosphine) sulfide (TOPS), tris (dimethylamino) arsine, an ammonium salt such as an ammonium halide (e.g., $NH_4Cl$), tris(trimethylsilyl) phosphide (($TMS)_3P$), tris(trimethylsilyl) arsenide (($TMS)_3As$), or tris (trimethylsilyl) antimonide (($TMS)_3Sb$). In certain embodiments, the M donor and the X donor can be moieties within the same molecule.

The nanocrystal manufactured from an M-containing salt grows in a controlled manner when the coordinating solvent includes an amine. The amine in the coordinating solvent contributes to the quality of the nanocrystal obtained from the M-containing salt and X donor. The coordinating solvent can be a mixture of the amine and an alkyl phosphine oxide in a mole ratio of, for example 10:90, 30:70, 50:50, 70:30, or 90:10. The combined solvent can decrease size dispersion and can improve photoluminescence quantum yield of the nanocrystal. The preferred amine is a primary alkyl amine or a primary alkenyl amine, such as a $C_2$-$C_{20}$ alkyl amine, a $C_2$-$C_{20}$ alkenyl amine, preferably a $C_8$-$C_{18}$ alkyl amine or a $C_8$-$C_{18}$ alkenyl amine. For example, suitable amines for combining with tri-octylphosphine oxide (TOPO) include 1-hexadecylamine, or oleylamine. When the 1,2-diol or aldehyde and the amine are used in combination with the M-containing salt to form a population of nanocrystals, the photoluminescence quantum efficiency and the distribution of nanocrystal sizes are improved in comparison to nanocrystals manufactured without the 1,2-diol or aldehyde or the amine.

The nanocrystal can be a member of a population of nanocrystals having a narrow size distribution. The nanocrystal can be a sphere, rod, disk, or other shape. The nanocrystal can include a core of a semiconductor material. The nanocrystal can include a core having the formula MX, where M is cadmium, zinc, magnesium, mercury, aluminum, gallium, indium, thallium, or mixtures thereof, and X is oxygen, sulfur, selenium, tellurium, nitrogen, phosphorus, arsenic, antimony, or mixtures thereof.

The nanocrystal can emit light when excited. The nanocrystal can be excited by irradiation with an excitation wavelength of light, by electrical excitation, or by other energy transfer, such as FRET. The emission from the nanocrystal can be a narrow Gaussian emission band that can be tuned through the complete wavelength range of the ultraviolet, visible, or infrared regions of the spectrum by varying the size of the nanocrystal, the composition of the nanocrystal, or both. For example, emission wavelengths of both CdSe and CdS can be tuned in the visible region and InAs can be tuned in the infrared region.

A population of nanocrystals can have a narrow size distribution. The population can be monodisperse and can exhibit less than a 15% rms deviation in diameter of the nanocrystals, preferably less than 10%, more preferably less than 5%. Spectral emissions in a narrow range of between 10 and 100 nm full width at half max (FWHM) can be observed. The FWHM, expressed in terms of energy, can be no greater than 0.05 eV, or no greater than 0.03 eV. Semiconductor nanocrystals can have emission quantum efficiencies of greater than 2%, 5%, 10%, 20%, 40%, 60%, 70%, or 80%.

The semiconductor forming the core of the nanocrystal can include Group II-VI compounds, Group II-V compounds, Group III-VI compounds, Group III-V compounds, Group IV-VI compounds, Group I-III-VI compounds, Group II-IV-VI compounds, and Group II-IV-V compounds, for example, ZnS, ZnSe, ZnTe, CdS, CdSe, CdTe, HgS, HgSe, HgTe, AlN, AlP, AlAs, AlSb, GaN, GaP, GaAs, GaSb, GaSe, InN, InP, InAs, InSb, TlN, TlP, TlAs, TlSb, PbS, PbSe, PbTe, or mixtures thereof.

The quantum efficiency of emission from nanocrystals having a core of a first semiconductor material be enhanced by applying an overcoating of a second semiconductor material such that the conduction band of the second semiconductor material is of higher energy than that of the first semiconductor material, and the valence band of the second semiconductor material is of lower energy than that of the first semiconductor material. As a result, carriers, i.e., electrons and holes, are confined in the core of the nanocrystal. The core can have an overcoating on a surface of the core. The overcoating can be a semiconductor material having a composition different from the composition of the core, and can have a band gap greater than the band gap of the core. The overcoat of a semiconductor material on a surface of the nanocrystal can include a Group II-VI compounds, Group II-V compounds, Group III-VI compounds, Group III-V compounds, Group IV-VI compounds, Group I-III-VI compounds, Group II-IV-VI compounds, and Group II-IV-V compounds, for example, ZnS, ZnSe, ZnTe, CdS, CdSe, CdTe, HgS, HgSe, HgTe, AlN, AlP, AlAs, AlSb, GaN, GaP, GaAs, GaSb, GaSe, InN, InP, InAs, InSb, TlN, TlP, TlAs, TlSb, PbS, PbSe, PbTe, or mixtures thereof. In certain examples, a second overcoating including a third semiconductor material can be present. Examples of nanocrystals include a ZnSe core having a first overcoating of CdSe and a second overcoating of ZnS (ZnSe/CdSe/ZnS), which can emit green light, or a CdZnS core having a first overcoating of ZnS, which can emit blue light. For example, these nanocrystals can be water solubilized through coupling of an amphiphilic polymer to the surface or cap exchange with dihydrolipoic acid modified caps, and can allow access to bluer wavelengths for FRET donor studies.

The nanocrystals described above can be water solubilized through both amphiphilic polymers and cap exchange with dihydrolipoic acid modified caps. They allow us to access bluer wavelengths for FRET donor studies.

An overcoating process is described, for example, in U.S. Pat. No. 6,322,901, incorporated herein by reference in its entirety. By adjusting the temperature of the reaction mixture during overcoating and monitoring the absorption spectrum of the core, over coated materials having high emission quantum efficiencies and narrow size distributions can be obtained. Alternatively, an overcoating can be formed by exposing a core nanocrystal having a first composition and first average diameter to a population of nanocrystals having a second composition and a second average diameter smaller than the first average diameter.

Size distribution during the growth stage of the reaction can be estimated by monitoring the absorption line widths of the particles. Modification of the reaction temperature in response to changes in the absorption spectrum of the particles allows the maintenance of a sharp particle size distribution during growth. Reactants can be added to the nucleation solution during crystal growth to grow larger crystals. By stopping growth at a particular nanocrystal average diameter, a population having an average nanocrystal diameter of less than 150 Å can be obtained. A population of nanocrystals can have an average diameter of 15 Å to 125 Å.

The particle size distribution can be further refined by size selective precipitation with a poor solvent for the nanocrystals, such as methanol/butanol as described in U.S. Pat. No. 6,322,901, incorporated herein by reference in its entirety. For example, nanocrystals can be dispersed in a solution of 10% butanol in hexane. Methanol can be added dropwise to this stirring solution until opalescence persists. Separation of supernatant and flocculate by centrifugation produces a precipitate enriched with the largest crystals in the sample. This procedure can be repeated until no further sharpening of the optical absorption spectrum is noted. Size-selective precipitation can be carried out in a variety of solvent/nonsolvent pairs, including pyridine/hexane and chloroform/methanol. The size-selected nanocrystal population can have no more than a 15% rms deviation from mean diameter, preferably 10% rms deviation or less, and more preferably 5% rms deviation or less.

Transmission electron microscopy (TEM) can provide information about the size, shape, and distribution of the nanocrystal population. Powder X-ray diffraction (XRD) patterns can provided the most complete information regarding the type and quality of the crystal structure of the nanocrystals. Estimates of size are also possible since particle diameter is inversely related, via the X-ray coherence length, to the peak width. For example, the diameter of the nanocrystal can be measured directly by transmission electron microscopy or estimated from X-ray diffraction data using, for example, the Scherrer equation. It also can be estimated from the UV/Vis absorption spectrum.

The outer surface of the nanocrystal can include a layer of compounds derived from the coordinating agent used during the growth process. The surface can be modified by repeated exposure to an excess of a competing coordinating group to form an overlayer. For example, a dispersion of the capped nanocrystal can be treated with a coordinating organic compound, such as pyridine, to produce crystals which disperse readily in pyridine, methanol, and aromatics but no longer disperse in aliphatic solvents. Such a surface exchange process can be carried out with any compound capable of coordinating to or bonding with the outer surface of the nanocrystal, including, for example, phosphines, thiols, amines and phosphates. The nanocrystal can be exposed to short chain polymers which exhibit an affinity for the surface and which terminate in a moiety having an affinity for a suspension or dispersion medium. Such affinity improves the stability of the suspension and discourages flocculation of the nanocrystal.

Monodentate alkyl phosphines (and phosphine oxides, the term phosphine below will refer to both) can passivate nanocrystals efficiently. Alternatively, thiol or disulfide-based compounds can be used as surface ligands. When nanocrystals with conventional monodentate ligands are diluted or embedded in a non-passivating environment (i.e. one where no excess ligands are present), they tend to lose their high luminescence and their initial chemical inertness. Typical are an abrupt decay of luminescence, aggregation, and/or phase separation. In order to overcome these limitations, polydentate ligands can be used, such as a family of polydentate oligomerized phosphine ligands or disulfide ligands, such as, for example, thioctic acid. The polydentate ligands show a high affinity between ligand and nanocrystal surface. In other words, they are stronger ligands, as is expected from the chelate effect of their polydentate characteristics. The ligand can include a hydrophilic group to enhance water solubility.

Oligomeric phosphines have more than one binding site to the nanocrystal surface, which ensures their high affinity to the nanocrystal surface. See, for example, for example, U.S. Ser. No. 10/641,292, filed Aug. 15, 2003, and U.S. Ser. No. 60/403,367, filed Aug. 15, 2002, each of which is incorporated by reference in its entirety. The oligomeric phosphine can be formed from a monomeric, polyfunctional phosphine, such as, for example, trishydroxypropylphosphine, and a polyfunctional oligomerization reagent, such as, for example, a diisocyanate. The oligomeric phosphine can be contacted with an isocyanate of formula R'-L-NCO, wherein L is $C_2$-$C_{24}$ alkylene, and R' has the formula

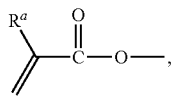

R' has the formula

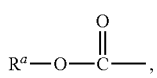

or R' is hydrogen, wherein $R^a$ is hydrogen or $C_1$-$C_4$ alkyl.

Alkyl is a branched or unbranched saturated hydrocarbon group of 1 to 100 carbon atoms, preferably 1 to 30 carbon atoms, such as methyl, ethyl, n-propyl, isopropyl, n-butyl, isobutyl, t-butyl, octyl, decyl, tetradecyl, hexadecyl, eicosyl, tetracosyl and the like, as well as cycloalkyl groups such as cyclopentyl, cyclohexyl and the like. Optionally, an alkyl can contain 1 to 6 linkages selected from the group consisting of —O—, —S—, and —NR— where R is hydrogen, or $C_1$-$C_8$ alkyl or lower alkenyl.

The outer surface can be modified without displacing the compounds derived from the coordinating agent used during the growth process. For example, when the coordinating solvent produces nanocrystals having a hydrophobic layer, such as a TOP/TOPO layer, the nanocrystals can be rendered water-soluble without displacing the TOP/TOPO layer. This can be achieved by exposing the nanocrystals to an amphiphilic compound, that is, a compound having hydrophobic and hydrophilic regions. The hydrophobic regions can associate with the TOP/TOPO layer while the hydrophilic regions are excluded from the TOP/TOPO layer. The amphiphilic compound can be a polymer, such as, for example, a block copolymer, a random copolymer, or a graft copolymer. The amphiphilic compound can be modified to include desired functional groups. For example, a polyacrylic acid can be modified by attaching alkyl groups (such as $C_6$-$C_{20}$ alkyl groups) to a portion of the carboxylic acid groups. The alkyl groups form a hydrophobic region that can associate with a hydrophobic layer on a nanocrystal, while the unmodified portion of carboxylic acid groups form a hydrophilic region that promotes water solubility.

Alternatively, the outer surface of the coordinating ligands can be exchanged, in part or completely, with a thiol-containing carboxylic acid compound such as, for example, thioctic acid. The carboxylic acid group can be coupled, for example, by activation as an N-hydroxysuccinimide (NHS) ester or through conversion to an isocyanate or thioisocyanate group, to other hydrophilic or multifunctional moieties. The hydrophilic or multifunctional moieties can be a polymer, for example, any amino or alcohol terminated polyalkylene glycol, such as a polyethylene glycol (PEG) or a dendrimer of any generation or size, such as, for example, a generation 1, generation 2, or generation 3 dendrimer, such as PAMAM.

With further reference to FIG. 1, linker 30 can be a covalent or non-covalent link. When linker 30 is a covalent link, linker 30 can include one or more coordinating groups that have an affinity for a nanocrystal surface. The coordinating groups can be selected from, for example, P, O=P, N, O=N, and S. A non-covalent link can rely on non-covalent interactions between a nanocrystal outer layer and second compound. For example, the nanocrystal outer layer can be hydrophobic and the second compound can be an amphiphilic compound. Alternatively, the nanocrystal outer layer can include a charged moiety that associates electrostatically with a charged moiety on the second compound. See, for example U.S. Patent Application Publication No. 2002/0182632. Linker 30 can be selected to maintain a distance between fluorescent moieties 20 and 40 that allows for efficient FRET.

Recognition moiety 45 can be selected to recognize any desired analyte. Analytes that can be detected by fluorescent sensors include: $H^+$ (i.e., pH), $Li^+$, $Na^+$, $K^+$, $Cs^+$, $Ag^+$, $Mg^{2+}$, $Ca^{2+}$, $Cu^{2+}$, $Zn^{2+}$, $Cd^{2+}$, $Hg^+$, $Pb^{2+}$, $Fe^{3+}$, histidine, $H_2PO_4^-$, $O_2$, carbohydrates (e.g., glucose or fructose), polypeptide N-terminal lysine, L-DOPA, GTP, $F^-$, inositol triphosphate, and nicotine. The fluorescent sensor can be modified to provide a desired functional group to facilitate linking to a semiconductor nanocrystal.

EXAMPLES

Figure 2A:
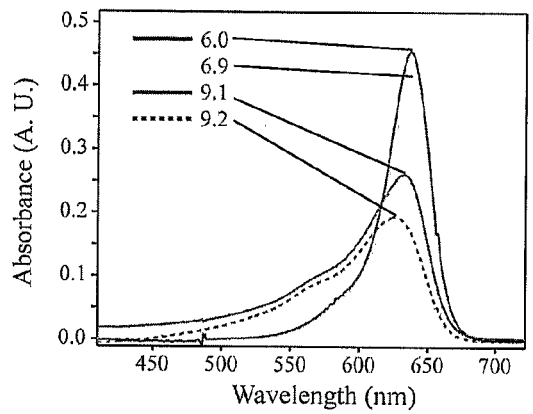
FIGS. 2A and 2B are graphs displaying optical properties of a fluorescent sensor.
Figure 2B:
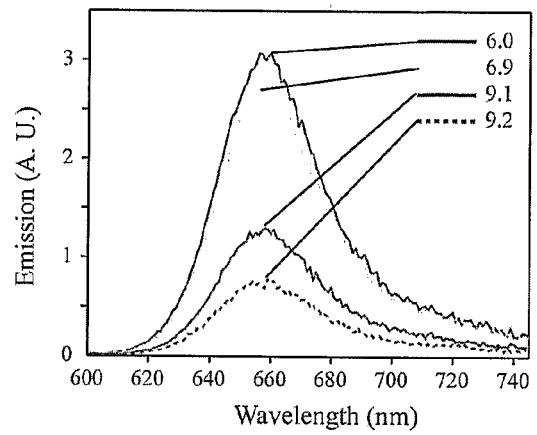

One example of a ratiometric, reversible semiconductor nanocrystal-based pH sensor is described below. A pH sensing dye was synthesized via a modified method, illustrated in Scheme 1 (see, e.g., Akkaya et al., *Tet. Lett.* 1997, 38, 7417-7420, which is incorporated by reference in its entirety). 3-benzyloxyaniline (1.99 g, 0.01 mol) was reacted with excess t-butylbromoacetate (5.906 mL, 0.04 mol) in the presence of a proton sponge (1,8-bis(dimethylamino)naphthalene) in acetonitrile. After purifying by flash chromatography, the bis-alkylated benzyloxyaniline product 1 was obtained. The benzyl protecting group of 1 (3.3188 g, 0.0063 mol) was deprotected by catalytic hydrogenation in the presence of Palladium/Carbon and purified by flash chromatography. The resulting product 2 (0.8846 g, 0.0024 mol) was reacted with 3,4-dihydroxy-3-cyclobutene-1,2-dione (squaric acid, 0.1420 g, 0.0012 mol) to yield a squaraine 3 as green needles. Trifluoroacetic acid deprotection of 3 (0.5089 g, 0.000647 mol) yielded the squaraine pH receptor dye 4, which was characterized by $^1$H NMR and UV-vis spectroscopy. FIGS. 2A and 2B present the absorbance and emission spectra, respectively, of the pH sensitive squaraine dye 4 as a function of pH.

CdSe nanocrystals overcoated with alloyed CdZnS were prepared using a modified literature method (see Fisher et al., *J. Phys. Chem. B,* 2004, 108, 143; and Dabbousi et al., *J. Phys. Chem. B.,* 1997, 101, 9463, each of which is incorporated by reference in its entirety). The core CdSe nanocrystals were prepared by a rapid injection of degassed solution comprised of 0.312 g cadmium 2,4-pentanedionate, 6 mL trioctylphosphine, 0.5 mL dodecanal, and 4 mL of a 1.0 M solution of trioctylphosphine selenide (TOPSe) in trioctylphosphine into a degassed solvent of 6.25 g trioctylphosphine oxide, 5.75 g hexadecylamine, and 3.4 mL trioctylphosphine at 360° C. The growing CdSe nanocrystals were then maintained at 240° C. until the desired emission wavelength was reached. The nanocrystals were overcoated by injecting a hexane solution of bare CdSe nanocrystals (prepared by size selected precipitation from the original growth solution) into a degassed solvent of 10 g trioctylphosphine oxide and 0.4 g n-hexylphosphonic acid. The hexane was removed in vacuo at 80° C., and 0.5 mL of decylamine was added. After stirring for 1 hr, the solution temperature was raised to 160° C. Over the course of 5 hours, two precursor solutions of (1) bis-(trimethylsilyl)sulfide in 5 mL trioctylphosphine and (2) a 80:20 molar ratio of diethylzinc and dimethylcadmium in 5 mL trioctylphosphine were slowly dripped in. Exact amounts were chosen to yield a 5 monolayer coating of CdZnS on the bare CdSe nanocrystals.

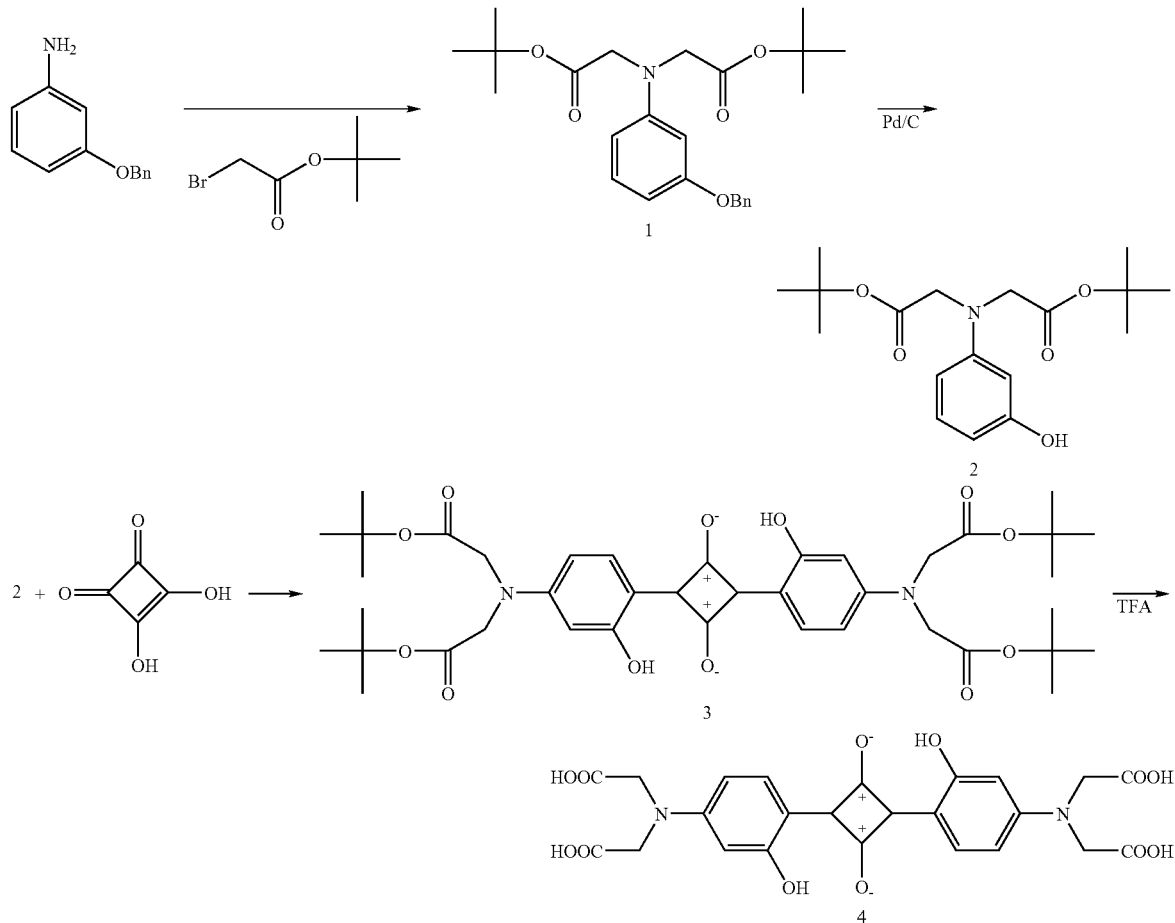

A functionalized polymer was synthesized by coupling a fraction (40%) of the carboxylic acid groups of a 1500 MW poly(acrylic acid) with octylamine using either 1-ethyl-3-(3-dimethylaminopropyl)-carbodiimide (EDC) or dicyclohexylcarbodiimide (DCC) in N,N-dimethylformamide. An additional 40% of the acid groups were coupled with 5-amino-1-pentanol, while the remaining 20% was left as free carboxylic acid. The functionalized polymer was purified by size-exclusion chromatography using Sephadex LH-20 with methanol as the mobile phase.

Water-soluble pH dye-nanocrystal conjugates were synthesized by sonicating a mixture of dried CdSe/CdZnS and polymer in ethanol for 1 hour, followed by removing the solvent in vacuo. A separate vial with 2 mg of the squaraine pH dye, 4 mgs of EDC, and 2.4 mgs of N-hydroxysuccinamide (NHS) was prepared in 1 mL of DMF and stirred for 10 minutes. To link the pH dye, polymer-coated nanocrystals were solubilized in 5 mL DMF, to which the squaraine pH dye solution was added and stirred overnight. Evaporation of DMF and addition of $H_2O$ and 0.1 mL 0.1 M tetrabutylammonium hydroxide in methanol yielded water-solubilized CdSe/CdZnS NC conjugated with the squaraine dye. The pH dye-nanocrystal conjugates were purified by dialysis through Millipore centrifuge tubes equipped with 50 kDa MW filters to remove any unreacted dye. After multiple washings, the free dye was completely removed from the conjugates, as verified by the absence of the parent dye absorption features in the UV-vis absorption spectrum of the filtrate.

Figure 3A:
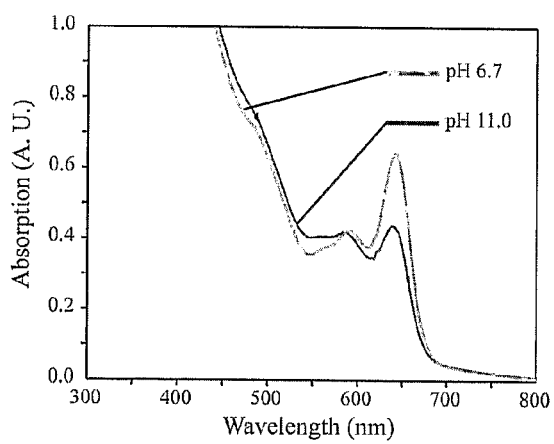
FIGS. 3A and 3B are graphs displaying optical properties of a fluorescent sensor.
Figure 3B:
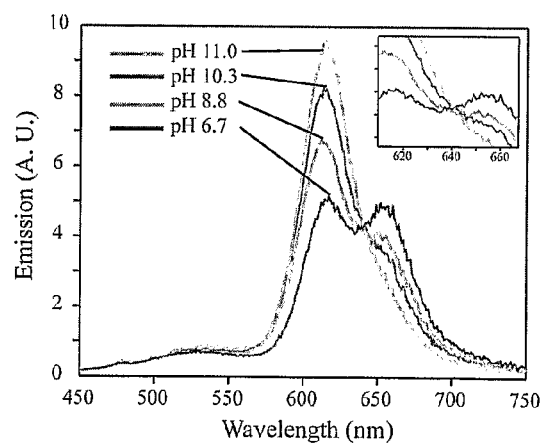

FIGS. 3A and 3B present the absorbance and emission spectra of the nanocrystal/pH sensitive squaraine dye conjugate as a function of pH. An isosbestic point is seen in the emission spectra at 640 nm.

In another example, the commercially available pH sensor SNARF (Molecular Probes Inc.) is attached in an analogous manner to a nanocrystal. Absorbance and emission spectra for this conjugate as a function of pH are presented in FIGS. 4A and 4B, respectively. These examples show that sensors that emit at several different wavelengths can be prepared.

A porphyrin-based oxygen sensor (Oxyphor R0, Pd-meso-tetra(4-carboxyphenyl) porphyrin) was similarly conjugated to a nanocrystal. The emission spectra of the conjugate as a function of $O_2$ level in solution was measured (see FIG. 5) The emission of the porphyrin was very sensitive to the presence of $O_2$ while the nanocrystal emission (see inset of FIG. 5), was not.

Figure 6:
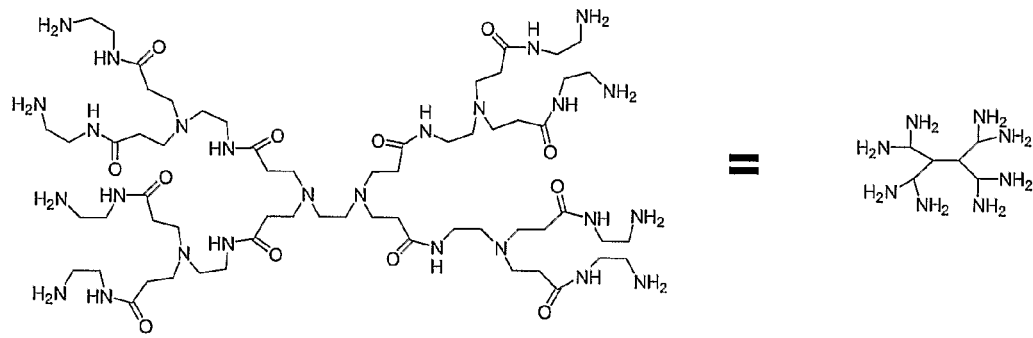
FIG. 6 is a schematic drawing depicting generation 1 of a dendrimer.
Figure 7:
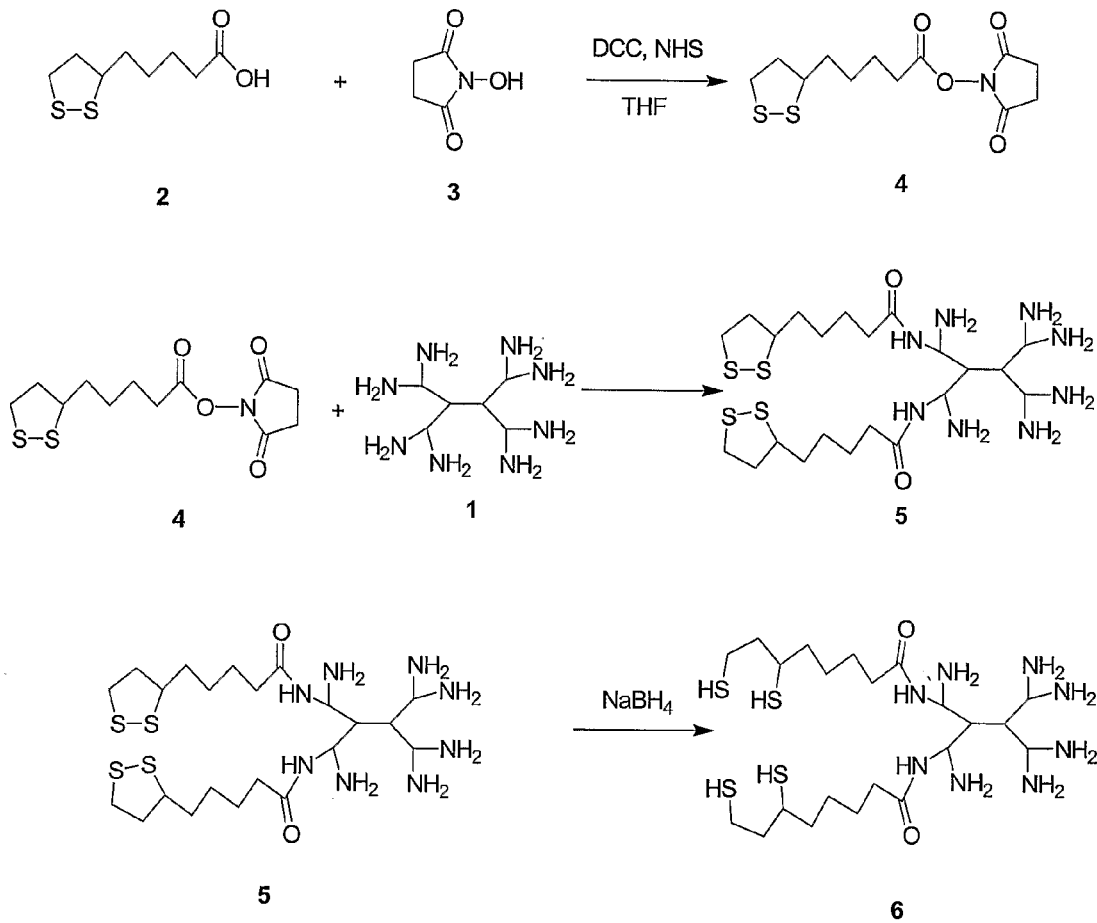
FIG. 7 is a schematic drawing depicting synthesis of a modified dendrimer.

In another example, synthesis of a nanocrystal surface capping ligand based on a dendrimer is shown in FIG. 7, which represents synthesis of a dihydrolipoic acid modified PAMAM dendrimer. One equivalent of thioctic acid, 2, was reacted with N-hydroxysuccinimide, 3, (NHS, 1.2 eq) in the presence of 1.2 eq. of N,N'-dicyclohexylcarbodiimide (DCC, 1.2 eq) in tetrahydrofuran (THF) to yield the NHS-ester of thioctic acid, 4. Two equivalents 4 is then reacted to 1 eq. of generation 1 poly(amido amine) (PAMAM) dendrimer, 1 whose core is ethylenediamine. For clarification (because of various naming conventions), the generation 1 poly(amido amine) with an ethylenediamine core is terminated with 8 amine groups per dendrimer, whose molecular weight is 1430. See, FIG. 6, which represents Generation 1 of a PAMAM dendrimer. The dendrimer, 1, contains 8 surface amine functionalities and will be subsequently be abbreviated as the figure to the right in future reaction schemes. The thioctic acid coupled dendrimer, 5, is subsequently reduced with excess sodium borohydride to yield dihydrolipoic acid coupled dendrimer, 6.

ZnSe/CdSe/ZnS nanocrystals were prepared for cap exchange with the dendrimer. The core ZnSe nanocrystals were prepared by a rapid injection of degassed solution comprised of 0.096 g of diethylzinc, 4 mL trioctylphosphine (TOP) and 1 mL of 1.0 M solution of trioctylphosphine selenide (TOPSe) into a degassed solvent of 7 g hexyldecylamine at 310° C. The growing of the ZnSe nanocrystals were then maintained at 270° C. until the desired emission wavelength was reached. The temperature was lowered to 150° C. The ZnSe were then overcoated with CdSe by injecting the bare ZnSe nanocrystals into a degassed solution of 8 g TOPO and 0.4 g of n-hecylphosphonic acid. Immediately after adding the ZnSe to the degassed TOPO solution, addition funnel containing degassed solutions of 4.4 mL TOP, 0.6 mL 1.5 TOPSe, and 0.078 g dimethylcadmium was allowed to drip, with a drip rate of approximately one drip per second. After the addition of the cadmium precursor mixture, the solution was stirred overnight. In order to overcoat the ZnSe/CdSe with ZnS, the ZnSe/CdSe was precipitated with methanol, and centrifuged to obtain a yellow paste as a precipitate. The nanocrystals were extracted out of the paste with hexanes until the paste was mostly white. The ZnSe/CdSe were subsequently precipitated from the hexane solutions twice with methanol and centrifuged. The resulting solid was then dissolved in a small amount of hexanes (4 mL) and injected to a degassed mixture of 10 g of distilled trioctylphosphine oxide (TOPO) and 0.4 g n-hexylphosphonic acid at 80° C. The hexane was removed in vacuo at 80° C., and 0.5 mL of decylamine was added under nitrogen. After stirring for 3 hours, the solution temperature was raised to 160° C. Over the course of three hours, two precursor solutions of (1) 0.13 g bis-(trimethylsilyl)sulfide in 5 mL TOP and (2) 0.035 g diethylzinc in 5 mL TOP were slowly dripped in to yield ZnSe/CdSe/ZnS green emitting nanocrystals.

The resulting ZnSe/CdSe/ZnS green emitting nanocrystals were exposed to thiolated dendrimer to exchange the capping group. The cap exchange took place using a modified literature method of Wisher et al., *Chem. Comm.* 2006, 1637, which is incorporated by reference in its entirety. Dried ZnSe/CdSe/ZnS (0.005 g) was dissolved in 60% chloroform/40% methanol solution and stirred. Thiolated dendrimer (0.2 g), 6, was added to the solution and stirred for three hours. Distilled and deionized water was then laid on top of the chloroform/methanol solution and slowly stirred. The mixture was left overnight to yield aqueous layer of nanocrystals on top, and a clear layer of chloroform/methanol on bottom. The aqueous layer was carefully pipetted out and purified by dialysis through Millipore centrifuge tubes equipped with 50 kDa MW filters to remove excess dendrimer.

The dendrimer encapsulated nanocrystals were then coupled to SNARF-pH dye as follows. A vial of 5 mg of SNARF®-5F 5-(and -6)-carboxylic acid (molecular probes), 8 mg of N-(3-Dimethylaminopropyl)-N'-ethylcarbodiimide (EDC), and 8 mg of sulfo-N-hydroxysuccinamide (S—NHS) was stirred in pH 6 MES buffer for 30 minutes. At the same time, the dendrimer encapsulated ZnSe/CdSe/ZnS was placed in pH 8.3 bicarbonate buffer. After 30 minutes, the SNARF solution was mixed in with the nanocrystal solution, with care being taken to ensure that the pH remained 8.3. The mixture was stirred overnight. Next, the SNARF-nanocrystal solution was stirred for 30 minutes at pH 11 to hydrolyze excess NHS esters, then purified by dialysis through Millipore centrifuge tubes equipped with 50 kDa MW filters until the free dye was completely removed from the nanocrystal-SNARF conjugates.

Figure 8:
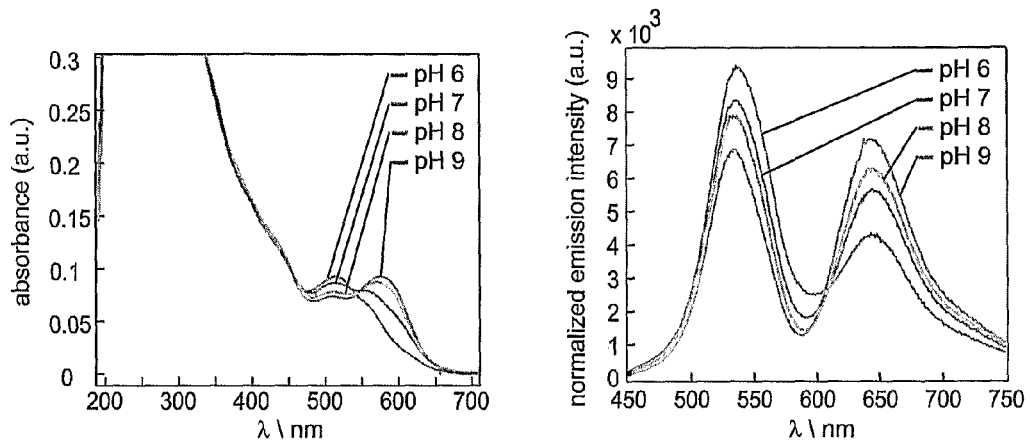
FIG. 8 is a pair of graphs depicting: (left) UV-vis absorption spectrum of a conjugate; and (right) steady-state fluorescence spectra of the conjugate.
Figure 9:
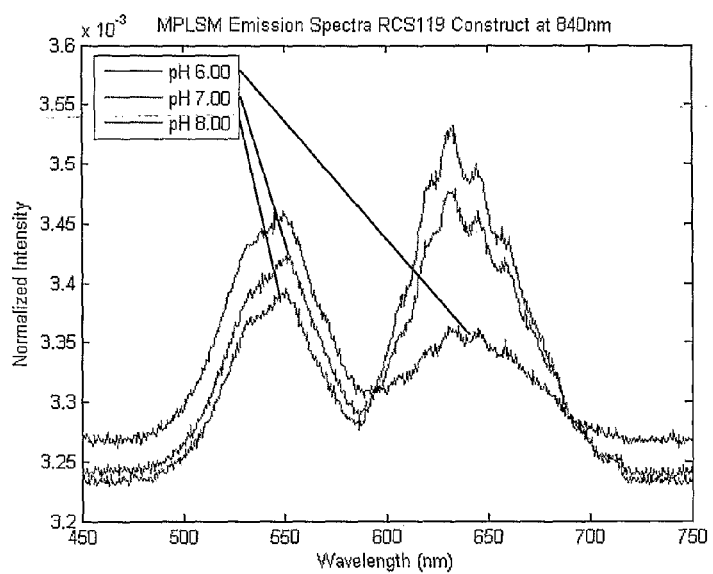
FIG. 9 is a graph depicting two-photon emission-profile of a conjugate.

The nanocrystal-SNARF conjugate photophysical data are shown in FIG. 8, which represents a pair of graphs depicting the UV-vis absorption spectrum of the nanocrystal-SNARF conjugate (left); and the steady-state fluorescence spectra of the nanocrystal-SNARF conjugate (right). The two photon emission profile of the nanocrystal-SNARF construct with 840 nm excitation obtained by MPLSM is shown in FIG. 9.

In another example, thioctic acid PEG cap-exchanged nanocrystals were prepared. Water-soluble nanocrystals were prepared through cap-exchanged ligands similar in a manner reported by Mattoussi and co-workers, Uyeda et al. *J. Am. Chem. Soc.* 2005; 127(11); 3870-3878, which is incorporated by reference in its entirety. Thioctic acid-NHS ester, 4, was prepared as described above. To the ester, 4, poly(propylene glycol)-block-poly(ethylene glycol)-block-poly(propylene glycol) bis(2-aminopropyl ether) (MW 600) was added in excess. The coupled amino-PEG was isolated, then reduced by sodium borohydride to give the dithiols.

Nanocrystals were isolated by repeated precipitation from hexanes by methanol and dried. To the dried nanocrystals, the dihydrolipoic acid-modified amino-PEG was added in excess and stirred at 60° C. overnight. The mixture was dissolved in methanol and precipitated with the addition of chloroform and hexanes. After decanting the supernatant, the nanocrystals were dissolved in water to yield water soluble nanocrystals.

Coupling to the dyes took place in a similar manner to the one described under the dendrimer encapsulated nanocrystals.

In another example, thioctic acid PEG cap-exchanged nanocrystals including nanocrystal-NHS esters were formed. Amine or hydroxyl terminated nanocrystals were prepared through formation of nanocrystal-NHS esters, with the subsequent coupling of a mono- or bis-amine terminated poly(ethylene glycol) (PEG).

Nanocrystals terminated with carboxylic acids through encapsulation by an amphiphilic polymer were subsequently reacted with an excess of EDC and NHS to form a nanocrystal-NHS precipitate. For example, 0.007 g of dried CdSe/ZnS core-shell nanocrystals was added to 0.035 g of octylamine modified poly(acrylic acid) in ethanol and sonicated for 1 hour, followed by removing the solvent in vacuo. The dried polymer-encapsulated nanocrystals were then dissolved in slightly basic water (pH 9), to which 0.1 g of EDC and 0.1 g of NHS were added. Following the addition of EDC and NHS, the nanocrystals precipitated out. The supernatant water was removed and the nanocrystals were briefly dried under vacuum. Addition of neat polypropylene glycol)-block-poly(ethylene glycol)-block-poly(propylene glycol) bis(2-aminopropyl ether) (MW 600) and subsequent stirring at 60° C. for 5 hours yielded amine terminated nanocrystals. Addition of water and subsequent dialysis in Millipore 50000 MW cutoff centrifuge filters until the filtrate remained free of excess free amino PEG ligand afforded the pure amino PEG terminated nanocrystals.

The same procedure was applicable to dihydrolipoic acid capped nanocrystals, which were prepared as reported by Mattoussi and co-workers in Uyeda et al. *J. Am. Chem. Soc.* 2005; 127(11); 3870-3878, which is incorporated by reference in its entirety. The dihydrolipoic acid capped nanocrystals dispersed in water were precipitated out with excess NHS and EDC. Subsequent immersion and stirring in neat amine terminated PEG at 60° C. for 5 hours, then addition of water and purification by dialysis afforded pure amine terminated nanocrystals with dihydrolipoic acid caps.

Both the polymer encapsulated amino PEG and dihydrolipoic acid capped amino PEG nanocrystals can be used to couple to dyes as described in the dendrimer section.

Other embodiments are within the scope of the following claims.

What is claimed is:

1. A composition comprising:
   a first fluorescent moiety;
   a second fluorescent moiety chemically bound to the first fluorescent moiety;
   wherein the first fluorescent moiety is capable of transferring energy to the second fluorescent moiety when excited, or the second fluorescent moiety is capable of transferring energy to the first fluorescent moiety when excited,
   the first fluorescent moiety is a semiconductor nanocrystal including a core including a first semiconductor material, one or more optional overcoatings including a second semiconductor material on a surface of the core, and an outer layer coated on the core or, if present, coated on the one or more optional overcoatings, and
   wherein the second fluorescent moiety is capable of binding an analyte.

2. The composition of claim 1, wherein the outer layer includes a compound linked to a surface of the core or, if present, the one or more optional overcoatings, and having a hydrophobic region.

3. The composition of claim 2, wherein the outer layer further comprises an amphiphilic compound having a hydrophobic region interacting via hydrophobic interactions with the hydrophobic region of the compound linked to a surface of the core or, if present, the one or more optional overcoatings.

4. The composition of claim 3, wherein the amphiphilic compound is linked to the second fluorescent moiety.

5. The composition of claim 3, wherein the amphiphilic compound is linked to a plurality of the second fluorescent moieties.

6. The composition of claim 5, wherein the amphiphilic compound is an amphiphilic polymer.

7. The composition of claim 1, wherein the semiconductor nanocrystal includes an overcoating including a second semiconductor material on a surface of the core.

8. The composition of claim 7, wherein the semiconductor nanocrystal includes a second overcoating on a surface of the overcoating including a third semiconductor material.

9. The composition of claim 1, wherein the outer layer includes an amphiphilic polymer.

10. The composition of claim 1, wherein the outer layer includes a polyethylene glycol or a dendrimer.

11. The composition of claim 1, wherein the core includes ZnSe or CdZnS.

12. The composition of claim 1, wherein the second fluorescent moiety is covalently or noncovalently bound to the first fluorescent moiety.

13. A method of detecting an analyte, comprising:
   illuminating a composition with an excitation wavelength, wherein the composition includes:
      a first fluorescent moiety;
      a second fluorescent moiety chemically bound to the first fluorescent moiety;
         wherein the first fluorescent moiety is capable of transferring energy to the second fluorescent moiety when excited, or the second fluorescent moiety is capable of transferring energy to the first fluorescent moiety when excited,
         the first fluorescent moiety is a semiconductor nanocrystal including a core including a first semiconductor material, one or more optional overcoatings including a second semiconductor material on a surface of the core, and an outer layer coated on the core or, if present, coated on the one or more optional overcoatings, and wherein the second fluorescent moiety is capable of binding an analyte; and measuring a fluorescent emission of the composition.

14. The method of claim 13, wherein measuring a fluorescent emission of the composition includes measuring a fluorescence emission intensity at an emission wavelength of the first fluorescent moiety.

15. The method of claim 13, wherein measuring a fluorescent emission of the composition includes measuring a fluorescence emission intensity at an emission wavelength of the second fluorescent moiety.

16. The method of claim 13, wherein measuring a fluorescent emission of the composition includes measuring a ratio of a fluorescence emission intensity of the first fluorescent moiety to a fluorescence emission intensity of the second fluorescent moiety.

17. The method of claim 16, further comprising relating the measured ratio to a concentration of the analyte.

18. The method of claim 13, wherein measuring a fluorescent emission of the composition includes determining a ratio between a fluorescence emission intensity of the first fluorescent moiety to a fluorescence emission intensity of the emissive isosbestic point for the composition or between a fluorescence emission intensity of the second fluorescent moiety to a fluorescence emission intensity of the emissive isosbestic point for the composition.

19. The method of claim 13, wherein measuring includes performing single-photon excited fluorescence microscopy or multi-photon laser scanning microscopy.

20. A method of making a composition comprising:

linking a first fluorescent moiety to a second fluorescent moiety, wherein the first fluorescent moiety is a semiconductor nanocrystal including a core including a first semiconductor material, one or more optional overcoatings including a second semiconductor material on a surface of the core, and an outer layer coated on the core or, if present, coated on the one or more optional overcoatings, and wherein the second fluorescent moiety is capable of binding an analyte.

21. The method of claim 20, wherein after linking the first fluorescent moiety, when excited, is capable of transferring energy to the second fluorescent moiety, or, when excited, the second fluorescent moiety is capable of transferring energy to the first fluorescent moiety.

22. The method of claim 20, wherein the outer layer includes a compound linked to a surface of the core or, if present, the one or more optional overcoatings, and having a hydrophobic region.

23. The method of claim 22, wherein linking includes contacting the semiconductor nanocrystal with an amphiphilic compound having a hydrophobic region.

24. The method of claim 23, further comprising linking the second fluorescent moiety to the amphiphilic compound.

25. The method of claim 24, wherein the amphiphilic compound is linked to the second fluorescent moiety.

26. The method of claim 20, wherein linking includes coupling a surface of the nanocrystal and the second fluorescent moiety with a polyethylene glycol or a dendrimer.

27. The method of claim 20, wherein linking includes contacting the semiconductor nanocrystal with a compound including a coordinating group having an affinity for a surface of the semiconductor nanocrystal, and a fluorescent moiety.

28. The method of claim 20, wherein the outer layer includes a compound having a first reactive functional group.

29. The method of claim 28, wherein linking includes contacting the semiconductor nanocrystal with a compound including a second reactive functional group capable of reacting with the first reactive functional group to form a bond, and a fluorescent moiety.

30. The method of claim 20, wherein the core includes ZnSe or CdZnS.

* * * * *

UNITED STATES PATENT AND TRADEMARK OFFICE
CERTIFICATE OF CORRECTION

| | | |
|---|---|---|
| PATENT NO. | : 8,101,430 B2 | Page 1 of 1 |
| APPLICATION NO. | : 11/990439 | |
| DATED | : January 24, 2012 | |
| INVENTOR(S) | : Preston T. Snee | |

It is certified that error appears in the above-identified patent and that said Letters Patent is hereby corrected as shown below:

In the Specifications:

Please delete the paragraph titled 'FEDERALLY SPONSORED RESEARCH OR DEVELOPMENT' encompassing column 1, lines 17-20:

"This invention was made with government support under Grant No. CHE0209898 awarded by the NSF, and grant number KK1043, awarded by the ARO. The government has certain rights in the invention."

and replace with:

--This invention was made with government support under Grant No. CHE0209898 awarded by the National Science Foundation and under Grant No. DAAD 19-03-D-0004 awarded by the Army Research Office. The government has certain rights in this invention.--

Signed and Sealed this
Fourth Day of December, 2012

David J. Kappos
*Director of the United States Patent and Trademark Office*